United States Patent [19]

Paakkinen et al.

[11] Patent Number: 4,930,346
[45] Date of Patent: Jun. 5, 1990

[54] METHOD FOR THE DETERMINATION OF THE PROPERTIES OF MOULDABLE MATERIALS, PARTICULARLY FOR THE DETERMINATION OF THE PLASTIC AND REOLOGIC PROPERTIES THEREOF

[75] Inventors: Ilmari Paakkinen, PPA 1 Moinsalmi SF-57230, Savonlinna, Finland; Erik T. Nordenswan, Oslo, Norway; Heikki O. Rantanen, Toijala, Finland

[73] Assignee: Ilmari Paakkinen, Savonlinna, Finland

[21] Appl. No.: 340,417

[22] PCT Filed: Sep. 24, 1987

[86] PCT No.: PCT/FI87/00129

§ 371 Date: Mar. 30, 1989

§ 102(e) Date: Mar. 30, 1989

[87] PCT Pub. No.: WO88/02481

PCT Pub. Date: Apr. 7, 1988

[30] Foreign Application Priority Data

Oct. 2, 1986 [FI] Finland .................................. 863993

[51] Int. Cl.$^5$ ...................... G01N 11/14; G01N 33/38
[52] U.S. Cl. .............................................. 73/59; 73/815
[58] Field of Search .............................. 73/59, 60, 815

[56] References Cited

U.S. PATENT DOCUMENTS 4,095,461  6/1978  Starita ................................... 73/815
4,343,190  8/1982  Danko et al. ...................... 73/60 X

FOREIGN PATENT DOCUMENTS 26839   9/1970  Japan ..................................... 73/59
868472  9/1981  U.S.S.R. ............................... 73/59

*Primary Examiner*—Hezron E. Williams
*Assistant Examiner*—Joseph W. Roskos
*Attorney, Agent, or Firm*—Cushman, Darby & Cushman

[57] ABSTRACT

A method for the determination of the properties of mouldable materials, such as the granular and pulverous masses of fresh concrete, and stiff liquids, particularly for the determination of the plastic and reologic properties thereof. A sample of a known weight is taken from the mass; the sample is subjected to a moulding effect; and a compression (S) and the number of working revolutions required therefor are determined. In order that the behavior of the material to be measured can be controlled accurately during the measuring process and that the obtained measuring results are accurate and reliable, the sample is compressed in two axially opposite directions with a constant force (P); the sample is moulded under a constant compression between two parallel inclined planes which change the rotationally change the direction of inclination thereof; the volume (V and $V_t$) of the sample is measured prior to the moulding and after a determined number of working revolutions (n); and the magnitude of the torque resisting the rotational change in direction of inclination of the inclined planes is measured from the sample at least at one determined shear speed of the sample, which shear speed depends on the revolving speed of the inclined planes and the angle of incline thereof.

8 Claims, 2 Drawing Sheets

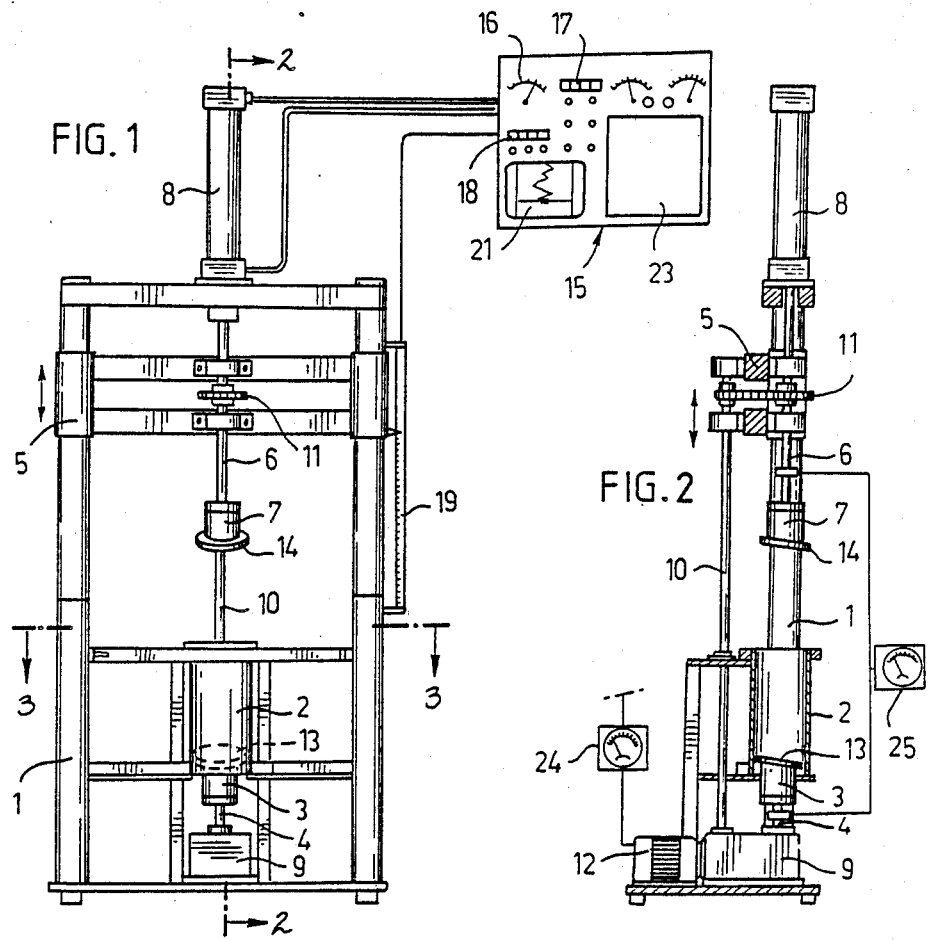

Ayah! 4,930,346

METHOD FOR THE DETERMINATION OF THE PROPERTIES OF MOULDABLE MATERIALS, PARTICULARLY FOR THE DETERMINATION OF THE PLASTIC AND REOLOGIC PROPERTIES THEREOF

A method for the determination of the properties of mouldable materials, particularly for the determination of the plastic and reologic properties thereof:

BACKGROUND OF THE INVENTION

This invention relates to a method for the determination of the properties of mouldable materials, such as the granular and pulverous masses of fresh concrete, and stiff liquids, particularly for the determination of the plastic and reologic properties thereof, in which method a sample of a known weight is taken from the mass,
the sample is subjected to a moulding effect, and
a compression of the sample and the number of working revolutions required therefor are determined.

Bingham's theory on the interdependence between the resistance to deformation and the shear speed of a material can be applied to plastic materials, such as concrete. According to this theory a plastic material has a yield ratio, i.e. a determined minimum shear stress, which is required for obtaining a permanent deformation, and a plastic viscosity dependent on the shear speed.

The measurement of the plastic and reologic properties, such as the yield ratio and the plastic viscosity, would be useful, because the behaviour of concrete both with respect to the castability and the compactibility thereof can be assessed by means of these values. Since the slump of a concrete cone is generally used to describe castability, it has to be taken into account that when using activated plasticizers or silica, the slump value has to be greater than in cases where these additives are not used if the same workability is to be achieved. This is due to the fact that such additives increase the plastic viscosity but not the yield ratio. In other words, concrete containing e.g. silica possesses a normal resistance to deformation at low speeds in slump measurements, but a high resistance at shear speeds occurring during vibration.

For measuring the plastic and reologic properties of plastic concrete masses with different shear speeds, a method is known in which concrete resting freely in a vessel is mixed with several different speeds and the force resisting the mixing is measured. The poorly controlled flows make it necessary to use a nonlinear speed scale. Thereby the shear speed field, too, is strongly non-homogenenous, and no accurate result can be obtained by the measurement if the concretes deviate greatly from each other. Consequently, not even plastic concrete masses can be measured reliably by means of this method.

SUMMARY OF THE INVENTION

The object of the present invention is to provide a method which avoids the above disadvantages and enables a more accurate measuring of the plastic and reologic properties of mouldable materials. This object is achieved by means of a method according to the invention which is characterized in that the sample is compressed in two opposite directions with a constant force; the sample is moulded under a constant compression between two parallel inclined planes which change position by revolving; the volume of the sample is measured prior to the compaction and after a determined number of working revolutions; and the magnitude of the torque resisting the revolving of the inclined planes is measured at least at one determined shear speed of the sample, which speed depends on the revolving speed of the inclined planes and the angle of incline thereof.

The invention is based on the concept that the determination of the plastic and reologic properties of a concrete mass is carried out by machine under accurately similar circumstances reproduceable for individual samples, whereby the information obtained on these properties is always reliable.

During the measuring process the shear speeds of the sample are accurately determined and homogenenous. This makes it possible to measure concrete samples in such a way that the obtained results are reliably reproduceable and physically controllable in view of the assessment of concrete.

By virtue of the method according to the invention it is possible to immediately alter the composition of the concrete mass to be prepared in a concrete mixer on the basis of the plastic and reologic properties measured from the sample so that the properties of a cast product will be as desired. In this way it is possible to avoid discarding of finished products and the waste work related thereto. The plastic and reologic properties of a stiff concrete mass can be studied equally accurately as previously in the case of plastic masses only. The method according to the invention is thus particularly suitable for the control of the manufacture of concrete products.

BRIEF DESCRIPTION OF THE DRAWINGS

The invention will be described in more detail in the following with reference to the attached drawings, wherein FIG. 1 is a front view of a structural detail of an apparatus used in the method according to the invention when in the filling position, FIGS. 2 and 3 are sectional views of the apparatus along the line 2—2 and the line 3—3, respectively, shown in FIG. 1, FIG. 4 is an enlarged view of an axial section of a compacting cylinder of the apparatus and the compacting pistons thereof when in the operating position.

DETAILED DESCRIPTION

Figure 5:
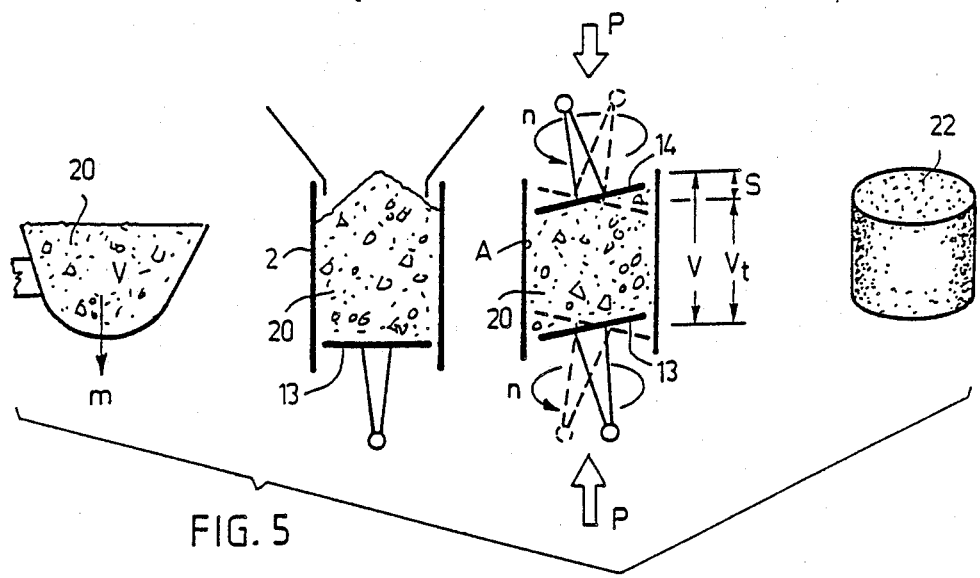
FIG. 5 shows the different operational stages of the method according to the invention.

The apparatus shown in FIGS. 1 to 4 comprises an upright compacting cylinder 2 supported on a frame 1, and a lower compacting piston 3 which closes the lower end of the cylinder and is fastened to a rotatable vertical shaft 4. A vertical shaft 6 is mounted rotatably in a carriage 5 mounted vertically slideably in the frame above the compacting cylinder. An upper compacting piston 7 is fastened to the vertical shaft 6 for closing the upper end of the compacting cylinder. The vertical shaft 6 is fastened to the piston arm of a hydraulic cylinder 8 mounted on the frame, which piston arm enables the carriage and the pistons thereof to be displaced in the vertical direction.

The seat of the frame supports a gear box 9 which is connected to the vertical shaft 4 of the lower compacting piston and to the vertical shaft 6 of the upper compacting piston by means of an intermediate shaft 10 and a transmission gear 11 so that both vertical shafts rotate with the same number of revolutions. The gear box comprises several different transmission ratios, and it is rotated by an electric motor 12.

Both compacting pistons define a round plate 13 and 14 respectively which has an inclined position with respect to the vertical shaft. Both pistons are mounted obliquely on the shafts so that the plates 13, 14 thereof are positioned in parallel with each other, as appears from FIGS. 1 and 2.

The apparatus comprises a meter board 15 comprising e.g. indicators 16 to 18 for the pressure of the hydraulic cylinder 8, for the number of revoltions of the compacting pistons and for the displacement of the carriage. A scale 19 is attached to the side of the frame for directly indicating the vertical position of the carriage. An electric torque measuring device 24, in turn, is attached to the electric motor 12, or an electric torque measuring device 25 is connected to the shafts 4 and 6.

FIG. 5 illustrates the measuring procedure to be carried out by means of the apparatus.

A sample 20 having a determined mass m is taken from a concrete mass. The sample is poured into the compacting cylinder 2, the cross-sectional area of which is F, and the upper compacting piston 7 is lowered on the sample. The piston is pressed against the sample by means of the hydraulic cylinder with a constant force P. Thereafter the pistons are rotated by means of the electric motor so that the obliquely mounted plates 13, 14 thereof exert a shear compaction effect on the sample. As a result thereof, the sample is compacted a distance S, also readable from the scale 19, after a determined number of revolutions n of the pistons, and the volume of the sample gets a value $V_t$. The magnitude of the torque resisting the revolving of the pistons during the revolving thereof is measured adjacent to the shafts rotating the pistons by means of the torque measuring device 25 or by means of the torque measuring device attached to the motor. The measurement is carried out at least at one determined shear speed of the sample; generally, however, at two different shear speeds. The shear speed of the sample depends of the angle speed $\omega$ of the shafts as well as on the angle of incline $\alpha$ of the plates 13 and 14 with respect to a straight line defined by the shafts 4 and 6, whereby a momentaneous maximum shear speed in a cross-section going through the axis of the cylinder is directly proportional to the product $\omega \cdot \sin \alpha$. The maximum shear speed is shifted according to the revolving movement so that this maximum shear speed is obtained during one revolution in any direction of observation. Since the plates 13 and 14 are always in parallel, the shear speed in an arbitrary cross-section equals to that in all parallel cross-sections, so that the shear speed field is completely homogenenous throughout the compacting cylinder 2. When the torque is measured at more than one shear speeds, the measurements are either carried out from the same sample by varying the shear speed during the measuring process, or a new sample is taken for each shear speed, whereby all the samples are identical. When two shear speeds are used, it is preferable that the second shear speed is 5 to 10 times greater than the first shear speed, which is of the order of 0.5 to 1 radian per second.

The yield ratio and the plastic viscosity of the sample, for instance, can be easily counted from the torque resisting the revolving of the pistons at different shear speeds.

The compacted sample can be utilized as a cylindrical test piece 22 from which the strength properties of the concrete can be measured after hardening.

Controlled by a freely selectable programme, the electric motor can be stopped at determined intervals for reading the numbers of revolutions n effected by the pistons and the respective slumps S. Alternatively, the electric motor may rotate continuously and the numbers of revolutions of the pistons and the slumps are transferred continuously to the memory of a process unit 23 for presenting the compactibility of the sample by means of a recorder 21.

By means of the method according to the invention it is possible to rapidly measure the reologic properties of a concrete mass to be prepared, i.e. in a few tens of minutes, thus obtaining reliable information on whether the concrete mass is suitable for the casting work in each particular case with a specific casting machine.

We claim:

1. A method for determining plastic and rheological properties of a moldable material, comprising:
   (a) taking a sample of known weight from a mass of a moldable material;
   (b) confining the sample in a mold having a sample-surrounding sidewall and two opposed pistons having respective axially-opposite inner end walls which define with said sidewall a mold cavity within which said sample is contained, said sidewall having a longitudinal axis, said inner end walls of said pistons being planar, parallel to one another and inclined at a given angle of inclination with respect to said longitudinal axis;
   (c) advancing one of said pistons relatively towards the other of said pistons until both said inner end walls engage said sample and said sample is subjected to a constant pressure;
   (d) while maintaining said constant pressure, coordinately changing the angle of inclination of said piston end surfaces by exerting a rotational force on said pistons, so that the magnitude of inclination of said end surfaces remains constant, but the direction each faces rotates around said longitudinal axis, whereby said pistons exert a shear compaction effect on said sample;
   (e) measuring from said sample the magnitude of the torque resisting said rotational force, at at least one predetermined shear speed, as an indication of plastic and rheological properties of said moldable material.

2. The method of claim 1, wherein:
said moldable material is a granular material.

3. The method of claim 1, wherein:
said moldable material is a pulverous mass.

4. The method of claim 1, wherein:
said moldable material is concrete which has not set.

5. The method of claim 1, wherein:
said moldable material is a stiff liquid.

6. The method of claim 1, wherein:
as step (d) and (e) are conducted said shear speed is changed so that the torque resisting the shear speed is measured for a plurality of different shear speeds.

7. The method of claim 1, wherein:
one said shear speed is in the range of 5 to 10 times greater than an earlier used one of said shear speeds.

8. The method of claim 1, wherein:
said earlier used one of said shear speeds is approximately 0.5 radians per second.

* * * * *